United States Patent
Cawthorne et al.

(10) Patent No.: US 7,256,174 B2
(45) Date of Patent: *Aug. 14, 2007

(54) SOMATOSTATIN AND SOMATOSTATIN AGONISTS FOR TREATING INSULIN INSENSITIVITY AND SYNDROME X

(75) Inventors: Michael Anthony Cawthorne, Horsham (GB); Yong-Ling Liu, Buckingham (GB); Matthew V. Sennitt, Shipstead (GB)

(73) Assignee: Societe de Conseils de Recherches et d'Applications Scientifiques, S.A.S., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/369,143

(22) Filed: Feb. 18, 2003

(65) Prior Publication Data

US 2004/0072734 A1    Apr. 15, 2004

Related U.S. Application Data

(60) Division of application No. 09/423,578, filed on Feb. 23, 2000, now abandoned, which is a continuation of application No. PCT/EP98/03000, filed on May 13, 1998, which is a continuation of application No. 08/854,943, filed on May 13, 1997, now abandoned.

(51) Int. Cl.
*A61K 38/00* (2006.01)
*C07K 1/00* (2006.01)

(52) U.S. Cl. .......... 514/16; 514/2; 514/9; 514/11; 530/328; 530/329; 530/317

(58) Field of Classification Search ............ 514/16, 514/2, 9, 11; 530/328, 329, 317
See application file for complete search history.

(56) References Cited

U.S. PATENT DOCUMENTS

| | | |
|---|---|---|
| 4,133,782 A | 1/1979 | Vale, Jr. et al. |
| 4,146,612 A | 3/1979 | Veber |
| 4,190,575 A | 2/1980 | Sarantakis |
| 4,190,648 A | 2/1980 | Veber |
| 4,209,426 A | 6/1980 | Sarantakis |
| 4,211,693 A | 7/1980 | Rivier et al. |
| 4,215,039 A | 7/1980 | Sarantakis |
| 4,224,199 A | 9/1980 | Meyers et al. |
| 4,235,886 A | 11/1980 | Freidinger et al. |
| 4,238,481 A | 12/1980 | Rink et al. |
| 4,261,885 A | 4/1981 | Sakakibara et al. |
| 4,282,143 A | 8/1981 | Sarantakis |
| 4,291,022 A | 9/1981 | Sandrin et al. |
| 4,310,518 A | 1/1982 | Freidinger et al. |
| 4,316,890 A | 2/1982 | Kamber et al. |
| 4,328,214 A | 5/1982 | Rink et al. |
| 4,358,439 A | 11/1982 | Sieber et al. |
| 4,360,516 A | 11/1982 | Freidinger et al. |
| 4,369,179 A | 1/1983 | Rink et al. |
| 4,395,403 A | 7/1983 | Bauer et al. |
| 4,435,385 A | 3/1984 | Bauer et al. |
| 4,485,101 A | 11/1984 | Coy et al. |
| 4,486,415 A | 12/1984 | Freidinger |
| 4,522,813 A | 6/1985 | Nutt |
| 4,585,755 A | 4/1986 | Morgan et al. |
| 4,603,120 A | 7/1986 | Kamber |
| 4,650,787 A | 3/1987 | Schally et al. |
| 4,684,620 A | 8/1987 | Hruby et al. |
| 4,725,577 A | 2/1988 | Schally et al. |
| 4,728,638 A | 3/1988 | Bauer et al. |
| 4,853,371 A | 8/1989 | Coy et al. |
| 4,871,717 A | 10/1989 | Coy et al. |
| 4,904,642 A | 2/1990 | Coy et al. |
| 5,506,339 A | 4/1996 | Coy et al. |
| 5,583,104 A | 12/1996 | LaRusso |
| 5,686,418 A | 11/1997 | Culler |
| 5,708,135 A | 1/1998 | Coy et al. |
| 5,763,200 A | 6/1998 | Dunmore et al. |

OTHER PUBLICATIONS

Van Bist et al., Peptide Research, vol. 5, No. 1, pp. 8-13, 1992.*
Hosker et al., "Continuous infusion of glucose with model assessment: measurement of insulin resistance and Beta-cell function in man" 1985, Diabetologia, vol. 28, pp. 401-411.*
Keith, et al., "u-Opioid Receptor Internalization: Opiate Drugs Have Differential Effects on a Conserved Endocytic Mechanism in vitro and in the Mammalian Brain," Mol. Pharmacology, 1998, 53:377-384.
Lunec, J. et al., MSH Receptor Expression and the Relationship to Melanogenesis and Metastatic Activity in B16 Melanoma,: Melanoma Research, 1992, 2:5-12.
Mak, K-H. et al., "Influence of Diabetes Mellitus on Clinical Outcome in the Thrombolytic Era of Acute Myocardial Infarction," JACC, 1997, 30(1):171-179.
Maruyama, Y. et al., "A Case of Insulin Dependent Diabetes Mellitus Following Systemic Treatment with Corticosteroids for Vogt-Koyanagi-Harada Syndrome," Ophthalmic Surgery and Lasers, 2000, 31(6):487-490.
McFayden, I. J. et al., "Modifications of the cyclic mu receptor selective tetrapeptide Tyr-c[D-Cys-Phe-D-Pen]NH$_2$ (Et): Effects on Opioid Receptor Binding and Activation," J. Peptide Res., 2000, 55:255-261.
Nasushita, R. et al., "A Case of Acromegaly Accompanied by Adrenal Preclinical Cushing's Syndrome," Endocrine Journal, 1999, 46(1):133-137.

(Continued)

Primary Examiner—Jon Weber
Assistant Examiner—Abdel A Mohamed
(74) Attorney, Agent, or Firm—Fish & Richardson; Alan F Feeney; Pamela C. Ball

(57) ABSTRACT

The present invention relates to a method of treating insulin resistance or Syndrome X by administering a therapeutically effective amount of a somatostatin agonist or a pharmaceutical composition comprised of a somatostatin agonist to a patient suffering from insulin resistance or Syndrome X.

5 Claims, No Drawings

OTHER PUBLICATIONS

O'Keefe, J. H. et al., "Improving the Adverse Cardiovascular Prognosis of Type 2 Diabetes," Mayo Clin. Proc., 1999, 74:171-180.

Torsello, A. et al., "Short Ghrelin Peptides Neither Displace Ghrelin Binding in vitro nor Stimulate GH Release in vivo," Endocrinology, 2002, 143(5):1968-1971.

Wandell, P. E. et al., "Drug Prescription in Diabetic Patients in Stockholm in 1992 and 1995—change over time," Eur. J. Clin. Pharmacol., 1997, 52:249-254.

Warner, D. P. et al., "Mortality and Diabetes from a population based register in Yorkshire 1978-1993," Arch. Dis. Child, 1998, 78:435-438.

Xiao, Q. et al., "Biological Activities of Glucagon-like Peptide-1 Analogues in vitro and in vivo," Biochemistry, 2001, 40:2860-2869.

Zuanetti, G. et al., "Influence of Diabetes on Mortality in Acute Myocardial Infarction: Data from the GISSI-2 Study," JACC, 1993, 22(7): 1788-1794.

* cited by examiner

SEQUENCE LISTING

```
<160> NUMBER OF SEQ ID NOS: 3

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: cyclo
      peptide
<220> FEATURE:
<223> OTHER INFORMATION: the N- and C-termini are joined together
      to form an amide bond

<400> SEQUENCE: 1

Pro Phe Trp Lys Thr Phe
  1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: cyclo
      peptide
<220> FEATURE:
<221> NAME/KEY: MOD_RES
<222> LOCATION: (3)
<223> OTHER INFORMATION: 5-fluorotryptophan
<220> FEATURE:
<223> OTHER INFORMATION: the N- and C-termini are joined together to
      form an amide bond

<400> SEQUENCE: 2

Pro Phe Xaa Lys Thr Phe
  1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: cyclo
      peptide
<220> FEATURE:
<221> NAME/KEY: MOD_RES
<222> LOCATION: (4)
<223> OTHER INFORMATION: 5-bromotryptophan
<220> FEATURE:
<221> NAME/KEY: MOD_RES
<222> LOCATION: (8)
<223> OTHER INFORMATION: gama-amino-n-butyric acid
<220> FEATURE:
<223> OTHER INFORMATION: the N- and C-termini are joined together to
      form an amide bond

<400> SEQUENCE: 3

Asn Phe Phe Xaa Lys Thr Phe Xaa
  1               5
```

SOMATOSTATIN AND SOMATOSTATIN AGONISTS FOR TREATING INSULIN INSENSITIVITY AND SYNDROME X

CROSS REFERENCE TO RELATED APPLICATIONS

Pursuant to 35 USC § 120, this application is a divisional of U.S. patent application Ser. No. 09/423,578, with a filing date of Feb. 23, 2000, now abandoned which is a continuation of International Patent Application No. PCT/EP98/03000, with an international filing date of May 13, 1998, which is a continuation of U.S. patent application Ser. No. 08/854,943, with a filing date of May 13, 1997 now abandoned.

This invention relates to a method and compositions for the treatment of insulin insensitivity and Syndrome X.

BACKGROUND OF THE INVENTION

Non-insulin-dependent diabetes mellitus (NIDDM) is highly prevalent in the U.S. population, reaching 10-20% in people 50 years and older. This incidence is higher among certain ethnic groups (Harris, M. I., Diabetes Care 16:642-652 (1993)). The condition is associated in the early phase with obesity, especially visceral and middle obesity. The progression from obesity to non-insulin dependent diabetes is characterized by the gradual development of insulin resistance occurring at least 4-7 years before clinical diagnosis of NIDDM (Harris, M. I., Diabetes Care 16:642-652 (1993); Harris, M. I., et al., Diabetes Care 15:815-819 (1992)). Insulin resistance is defined as the decrease in the biological action of insulin on the classical insulin sensitive tissues, namely muscle and liver leading to a reduced uptake and utilization of glucose from the bloodstream. In response to the reduced actions of insulin, the mounting plasma glucose induces the pancreas to put out more insulin leading to a higher basal circulating levels of the hormone in the interprandial state. Thus, insulin resistance often presents as hyperinsulinemia (Bonner, G., J Cardiovascular Pharmacology 24(Suppl. 2):S39-S49) (1994)). Initially, the higher circulating levels of insulin compensate for the reduced sensitivity to the hormone. As the pancreas decompensates and becomes unable to keep up with the demand, a fragile metabolic state of impaired glucose tolerance results. In this state, the organism is unable to handle a high influx of glucose into the bloodstream, for example after a meal or to a glucose challenge. This typically demonstrated by the slow rate in normalizing plasma glucose after a meal compared to normal individuals. It is at this point that non-insulin-dependent diabetes is usually diagnosed.

The period of some 5-10 years proceeding the development of impaired glucose tolerance is thus associated with a number of hormonal imbalances, e.g., increased basal insulin and glucagon production, elevated adrenal corticoid secretion (Bjornstop, P., In: Current Topics in Diabetes Research, eds. Belfore, F., Bergman, R N, and Molinath, G M, Front Diabetes, Basel, Karger, 12:182-192 (1993)), giving rise to the characteristic enlargement of visceral fat mass, hypertension, insulin resistance, and hyperlipidemia.

The cluster of these metabolic abnormalities has been referred to as "Syndrome X", "Metabolic Syndrome", "insulin resistant syndrome", or "Plurimetabolic Syndrome" (Reaven, G. M., Diabetes 37:1595-1607 (1988); Branchi, R., et al., Diab. Nutr. Metab. 7:43-51 (1994)). The condition was also shown to be associated with an increased risk for atherosclerosis, and coronary heart disease (reviewed in Wajchenberg, B. L., et al., Diabetes/Metabolism Reviews 10:19-29 (1994); Reaven, G. M., J. Int. Med. 236(Suppl. 736) :134-22 (1994); Woods, J. E., Ann. Intern. Med. 13:81-90 (1939); Modan, A., et al., J. Clin. Invest. 75:809-817 (1985)). Although the causal relationship between the various metabolic components remains to be confirmed (Donahue, R. P., The Endocrinologist 4:112-116 (1994); Fontbonne, A., Circulation 88(4 Pt.1):1952-1953 (1993); Jarrett, R. J., Diabetologia 37:945-947 (1994); Reaven, G. M., et al., Diabetologia 37:948-952 (1994); McCarty, M. F., Medical Hypothesis 42:226-236 (1994); Feskens, E. J. M., et al., Arteriosclerosis and Thrombosis 14:1641-1647 (1994)), insulin resistance appears to play an important role (Requen, G. M., et al., N. Eng. J. Med. 334:374-381 (1996); Despres, J-P., et al., N. Engl. J. Med. 334:952-957 (1996); Wajchenberg, B. L., et al., Diabetes/Metabolism Rev. 10:19-29 (1994)). There are no approved or confirmed effective treatments for the "insulin resistant syndrome" or "Syndrome X". Emerging data suggest that a number of therapies currently approved for the management of NIDDM may alleviate insulin resistance, e.g., Metformin (DeFronzo, R. A., et al., N. Eng. J. Med. 333:541-549 (1995)), Troghtazone (Kumar, S., et al., Diabetologia 39:701-709 (1996).

There is preliminary evidence in humans that acute infusion of somatostatin in obese hyperinsulinemic hypertensive patients resulted in a transient decrease in mean arterial blood pressure (Carretta, R., et al., J. Hypertension 7(suppl 6) :S196-S197 (1989)). Although this study pointed to a potential role of somatostatin in the management of hypertension associated with obesity, hypertension is only one of the clinical outcomes in the constellation of abnormalities associated with Syndrome X (Wajchenberg, B. L., et al., Diabetes/Metabolism Rev. 10:19-29 (1994)). A role of insulin is also implicated in the study. The involvement of insulin remains controversial as an acute increase in plasma insulin after a meal is typically associated with a reduction in blood pressure. Also, prolonged maintenance of hyperinsulinemia in animals does not raise blood pressure (McCarty, M. F., Medical Hypothesis, 1994, 42, 226-236). Also, epidemiologic studies have not yielded a clear-cut association between hyperinsulinemia and the risk for coronary heart disease (Jarrett, R. S., Diabetologia 37:945-947 (1994); Giuliano, D., et al., J. Endocrinol. Invest. 17:391-396 (1991); Feskens, E. J. M., Arterioscler. Thromb. 14:1641-1647 (1994); Ohmori, S., et al., J. Hypertension 12:1191-1197 (1994); Reaven, G. M., Diabetologia 37:948-592 (1994)).

The effect of somatostatin is mediated by a family of five somatostatin receptor isotypes. The current invention identifies a salient role of somatostatin agonists (e.g., somatostatin type-5 agonists) for the management of insulin resistance and Syndrome X as well as the normalization of metabolic changes that could mitigate development of disorders associated with Syndrome X, i.e. hyperlipidemia, insulin resistance and hyperinsulinemia.

SUMMARY OF THE INVENTION

The present invention relates to a method of treating insulin resistance and/or syndrome X in a patient (e.g., a mammal such as a human). The method includes the step of administering a therapeutically effective amount of somatostatin or a somatostatin agonist (e.g., a type-5 somatostatin receptor agonist or a type-5 somatostatin receptor selective agonist) to said patient. The somatostatin or somatostatin agonist may be administered parenterally, e.g., administered intravenously, subcutaneously, or by implantation of a sustained release formulation. In one embodiment, the patient is obese (e.g., as defined by body mass index (BMI) greater than 25% over normal and including risk factors or a BMI greater than 30% over normal (Bray, G A and Gray, D S, Diabetes/Metabolism Review 4:653-679 (1988)).

The invention also provides a pharmaceutical composition comprising a therapeutically effective amount of a somatostatin; or a somatostatin agonist or H-Cys-Phe-D-Trp-Lys-Thr-Phe-Cys-NH$_2$, wherein a disulfide bond exists between the free thiols of the two Cys residues. Also the invention provides the use of such products in the production of such composition for the treatment of insulin resistance and/or Syndrome X in a human or mammalian animal.

Definition of "somatostatin agonist" will be defined below. A therapeutically effective amount depends upon the condition being treated, the route of administration chosen, and the specific activity of the compound used and ultimately will be decided by the attending physician or veterinarian (e.g., between 5 μg/day to 5 mg/day). In one embodiment, the somatostatin agonist is administered to the patient until the patient is no longer insulin resistant or no longer suffering from syndrome X (e.g., the patient has restored insulin sensitivity). In another embodiment, the somatostatin agonist is administered for the lifetime of the patient (e.g., maintaining insulin sensitivity). The effect of the somatostatin agonists on Syndrome X may be determined by an improvement in insulin sensitivity (see, e.g., Turner, Rn. C., et al., Diabetes 44:1-10 (1995)) as well as a lowering of plasma lipids (see, e.g., Dubrey, S. W., et al., Diabetes 43:831-835 (1994)), blood pressure (Maheux, P., Hypertension 695:698 (1994)), and a change in body fat distribution (see, e.g., Zamboni, M., et al., Amer. J. Clin. Nutr. 60:682-687 (1994)).

What is meant by "insulin resistant" or "insulin resistance" in a patient is a decrease in the biological action of insulin in vivo as assessed by the rate of disposal of glucose from the bloodstream (e.g., into insulin-sensitive tissue, such as muscle, fat and liver) This assessment is evaluated clinically by an assessment of tolerance to a glucose challenge either orally or via the intravenous route (e.g., as described in Turner, R., et al., Diabetes 44:1-10 (1995)). Various techniques have been used to directly assess the rate of glucose removal, the euglycemic and hyperglycaemic clamp, the Minimal model and the Homeostasis model (see, e.g., Bergman, R. N., et al., Endocrin. Rev. 6:45-86 (1985); Duysim, B. C., et al., Diabets & Metab. 20:425-432 (1994); Katz, H., et al., Diabetes 43:289-296 (1994); Hosker, J. P., et al., Diabetologia 28:401-411 (1995)).

What is meant by "Syndrome X" is a metabolic disease characterized by insulin resistance with possible secondary abnormalities of obesity, hypertension, increased circulatory levels of triglycerides containing very low density lipoproteins (VLDLs), and a reduction in high density lipoprotein (HDL) cholesterol.

The somatostatin agonist may be injected parenterally, e.g., intravenously, into the bloodstream of the subject being treated. However, it will be readily appreciated by those skilled in the art that the route, such as intravenous, subcutaneous, intramuscular, intraperitoneal, enterally, transdermally, transmucously, sustained released polymer compositions (e.g., a lactic acid polymer or copolymer microparticle or implant), profusion, nasal, oral, etc., will vary with the condition being treated and the activity and bioavailability of the somatostatin agonist being used.

While it is possible for the somatostatin agonist to be administered as the pure or substantially pure compound, it may also be presented as a pharmaceutical formulation or preparation. The formulations to be used in the present invention, for both humans and animals, comprise any of the somatostatin agonists to be described below, together with one or more pharmaceutically acceptable carriers thereof, and optionally other therapeutic ingredients.

The carrier must be "acceptable" in the sense of being compatible with the active ingredient(s) of the formulation (e.g., capable of stabilizing peptides) and not deleterious to the subject to be treated. Desirably, the formulation should not include oxidizing agents or other substances with which peptides are known to be incompatible. For example, somatostatin agonists in the cyclized form (e.g., internal cysteine disulfide bond) are oxidized; thus, the presence of reducing agents as excipients could lead to an opening of the cysteine disulfide bridge. On the other hand, highly oxidative conditions can lead to the formation of cysteine sulfoxide and to the oxidation of tryptophan. Consequently, it is important to carefully select the excipient. pH is another key factor, and it may be necessary to buffer the product under slightly acidic conditions (pH 5 to 6).

The formulations may conveniently be presented in unit dosage form and may be prepared by any of the methods well known in the art of pharmacy. All methods include the step of bringing the active ingredient(s) into association with the carrier which constitutes one or more accessory ingredients.

In general, the formulations for tablets or powders are prepared by uniformly and intimately blending the active ingredient with finely divided solid carriers, and then, if necessary, as in the case of tablets, forming the product into the desired shape and size.

Formulations suitable for parenteral (e.g., intravenous) administration, on the other hand, conveniently comprise sterile aqueous solutions of the active ingredient(s). Preferably, the solutions are isotonic with the blood of the subject to be treated. Such formulations may be conveniently prepared by dissolving solid active ingredient(s) in water to produce an aqueous solution, and rendering said solution sterile. The formulation may be presented in unit or multi-dose containers, for example, sealed ampoules or vials.

Formulations suitable for sustained release parenteral administrations (e.g., biodegradable polymer formulations such as polyesters containing lactic or glycolic acid residues) are also well known in the art. See, e.g., U.S. Pat. Nos. 3,773,919 and 4,767,628 and PCT Publication No. WO 94/15587.

The somatostatin or somatostatin agonist may also be administered with other agents such as thiazoladinedione (e.g., trogliterazone), bromocriptine, B3-adrenergic agonists, and metformin.

Other features and advantages of the invention will be apparent from the following description of the preferred embodiments and from the claims.

Abbreviations

β-Nal=β-naphthylalanine
β-Pal=β-pyridylalanine
hArg(Bu)=N-guanidino-(butyl)-homoarginine
harg (Et)$_2$=N,N'-guanidino-(dimethyl)-homoarginine
harg(CH$_2$CF$_3$)$_2$=N,N'-guanidino-bis-(2,2,2,-trifluoroethyl)-homoarginine
hArg(CH$_3$, hexyl)=N,N'-guanidino-(methyl, hexyl)-homoarginine
Lys(Me)=N$^\epsilon$-methyllysine
Lys(iPr)=N$^\epsilon$-isopropyllysine
AmPhe=aminomethylphenylalanine
AChxAla=aminocyclohexylalanine Abu=α-aminobutyric acid
Tpo=4-thiaproline
MeLeu=N-methylleucine
Orn=ornithine
Nle=norleucine
Nva=norvaline
Trp(Br)=5-bromo-tryptophan
Trp(F)=5-fluoro-tryptophan
Trp(NO$_2$)=5-nitro-tryptophan
Gaba=γ-aminobutyric acid
Bmp=β-mercaptopropionyl
Ac=acetyl
Pen=pencillamine

DETAILED DESCRIPTION OF THE INVENTION

It is believed that one skilled in the art can, based on the description herein, utilize the present invention to its fullest extent. The following specific embodiments are, therefore, to be construed as merely illustrative, and not limitative of the remainder of the disclosure in any way whatsoever.

Unless defined otherwise, all technical and scientific terms used herein have the same meaning as commonly understood by one of ordinary skill in the art to which this invention belongs. Also, all publications, patent applications, patents, and other references mentioned herein are incorporated by reference.

Somatostatin and its Agonists

Somatostatin (somatotropin release inhibiting factor or SRIF) has both a 14 amino acid isoform (somatostatin-14) and a 28 amino acid isoform (somatostatin-28). See Wilson, J. & Foster, D., Williams *Textbook of Endocrinology*, p. 510 (7th ed., 1985). The compound is an inhibitor of secretion of the growth hormone and was originally isolated from the hypothalamus. Brazeau, et al., Science 179:77 (1973). Native somatostatin has a very short duration of effect in vivo since it is rapidly inactivated by endo- and exopeptidase. Many novel analogs have been prepared in order to enhance the duration of effect, biological activity, and selectivity (e.g., for the particular somatostatin receptor) of this hormone. Such analogs will be called "somatostatin agonists" herein.

Various somatostatin receptors (SSTRs) have been isolated, e.g., SSTR-1, SSTR-2, SSTR-3, SSTR-4, and SSTR-5. Thus, the somatostatin agonist may be a SSTR-1 agonist, SSTR-2 agonist, SSTR-3 agonist, SSTR-4 agonist or an SSTR-5 agonist. In one embodiment, the somatostatin agonist of the present invention is an SSTR-5 agonist or an SSTR-2 agonist. What is meant by an "SSTR-5 agonist" or an "SSTR-2 agonist" is a compound which (1) has a high affinity (e.g., Ki of less than 1 μM or, preferably, of less than 10 nM, or less than 2 nM, or of less than 1 nM) for the SSTR-5 or SSTR-2, respectively (e.g., as defined by the receptor binding assay described below), and (2) decreases body weight of a patient (e.g., as defined by the biological assay described below). The somatostatin agonist may also be selective for a particular somatostatin receptor, e.g., have a higher binding affinity for a particular somatostatin receptor subtype as compared to the other receptor subtypes. In one embodiment, the somatostatin receptor is an SSTR-5 selective agonist or SSTR-2 selective agonist. What is meant by an SSTR-5 selective agonist is a somatostatin agonist which (1) has a higher binding affinity (i.e., Ki) for SSTR-5 than for either SSTR-1, SSTR-2, SSTR-3, or SSTR-4 and (2) decreases body weight of a patient (e.g., as defined by the biological assay described below). In one embodiment, the SSTR-5 selective agonist has a Ki for SSTR-5 that is at least 2 times (e.g., at least 5 times or at least 10 times) less than its Ki for the SSTR-2 receptor (e.g., as defined by the receptor binding assay described below).

Somatostatin agonists which can be used to practice the therapeutic method of the present invention include, but are not limited to, those covered by formulae or those specifically recited in the publications set forth below, all of which are hereby incorporated by reference.

EP Application No. P5 164 EU (Inventor: G. Keri);
Van Binst, G. et al. Peptide Research 5:8 (1992);
Horvath, A. et al. Abstract, "Conformations of Somatostatin Analogs Having Antitumor Activity", 22nd European peptide Symposium, Sep. 13-19, 1992, Interlaken, Switzerland;
PCT Application Wo 91/09056 (1991);
EP Application 0 363 589 A2 (1990);
U.S. Pat. No. 4,904,642 (1990);
U.S. Pat. No. 4,871,717 (1989);
U.S. Pat. No. 4,853,371 (1989);
U.S. Pat. No. 4,725,577 (1988);
U.S. Pat. No. 4,684,620 (1987)
U.S. Pat. No. 4,650,787 (1987);
U.S. Pat. No. 4,603,120 (1986);
U.S. Pat. No. 4,585,755 (1986);
EP Application 0 203 031 A2 (1986);
U.S. Pat. No. 4,522,813 (1985);
U.S. Pat. No. 4,486,415 (1984);
U.S. Pat. No. 4,485,101 (1984);
U.S. Pat. No. 4,435,385 (1984);
U.S. Pat. No. 4,395,403 (1983);
U.S. Pat. No. 4,369,179 (1983);
U.S. Pat. No. 4,360,516 (1982);
U.S. Pat. No. 4,358,439 (1982);
U.S. Pat. No. 4,328,214 (1982);
U.S. Pat. No. 4,316,890 (1982);
U.S. Pat. No. 4,310,518 (1982);
U.S. Pat. No. 4,291,022 (1981);
U.S. Pat. No. 4,238,481 (1980);
U.S. Pat. No. 4,235,886 (1980);
U.S. Pat. No. 4,224,190 (1980);
U.S. Pat. No. 4,211,693 (1980);
U.S. Pat. No. 4,190,648 (1980);
U.S. Pat. No. 4,146,612 (1979);
U.S. Pat. No. 4,133,782 (1979);
U.S. Pat. No. 5,506,339 (1996);
U.S. Pat. No. 4,261,885 (1981);
U.S. Pat. No. 4,728,638 (1988);
U.S. Pat. No. 4,282,143 (1981);
U.S. Pat. No. 4,215,039 (1980);
U.S. Pat. No. 4,209,426 (1980);
U.S. Pat. No. 4,190,575 (1980);
EP Patent No. 0 389 180 (1990);
EP Application No. 0 505 680 (1982);
EP Application No. 0 083 305 (1982);
EP Application No. 0 030 920 (1980);
PCT Application No. WO 88/05052 (1988);
PCT Application No. WO 90/12811 (1990);
PCT Application No. WO 97/01579 (1997);
PCT Application No. WO 91/18016 (1991);
U.K. Application No. GB 2,095,261 (1981); and
French Application No. FR 2,522,655 (1983).

Examples of somatostatin agonists include, but are not limited to, the following somatostatin analogs which are disclosed in the above-cited references:

H-D-β-Nal-Cys-Tyr-D-Trp-Lys-Thr-Cys-Thr-NH$_2$ (BIM-23014);
H-D-Phe-Cys-Phe-D-Trp-Lys-Thr-Cys-β-Nal-NH$_2$;
H-D-Phe-Cys-Tyr-D-Trp-Lys-Thr-Cys-β-Nal-NH$_2$;
H-D-β-Nal-Cys-Phe-D-Trp-Lys-Thr-Cys-Thr-NH$_2$;
H-D-Phe-Cys-Tyr-D-Trp-Lys-Thr-Pen-Thr-NH$_2$;
H-D-Phe-Cys-Phe-D-Trp-Lys-Thr-Pen-Thr-NH$_2$;
H-D-Phe-Cys-Tyr-D-Trp-Lys-Thr-Pen-Thr-OH;
H-D-Phe-Cys-Phe-D-Trp-Lys-Thr-Pen-Thr-OH;
H-Gly-Pen-Phe-D-Trp-Lys-Thr-Cys-Thr-OH;
H-Phe-Pen-Tyr-D-Trp-Lys-Thr-Cys-Thr-OH;
H-Phe-Pen-Phe-D-Trp-Lys-Thr-Pen-Thr-OH;
H-D-Phe-Cys-Phe-D-Trp-Lys-Thr-Cys-Thr-ol (Octreotide);
H-D-Phe-Cys-Phe-D-Trp-Lys-Thr-Cys-Thr-NH$_2$;
H-D-Trp-Cys-Tyr-D-Trp-Lys-Val-Cys-Thr-NH$_2$;
H-D-Trp-Cys-Phe-D-Trp-Lys-Thr-Cys-Thr-NH$_2$;
H-D-Phe-Cys-Tyr-D-Trp-Lys-Val-Cys-Thr-NH$_2$;
H-D-Phe-Cys-Tyr-D-Trp-Lys-Val-Cys-Trp-NH$_2$;
H-D-Phe-Cys-Tyr-D-Trp-Lys-Val-Cys-Phe-NH$_2$;
Ac-D-Phe-Lys*-Tyr-D-Trp-Lys-Val-Asp-Thr-NH$_2$ (an amide bridge formed between Lys* and Asp);
Ac-hArg(Et)$_2$-Gly-Cys-Phe-D-Trp-Lys-Thr-Cys-Thr-NH$_2$;
Ac-D-hArg(Et)$_2$-Gly-Cys-Phe-D-Trp-Lys-Thr-Cys-Thr-NH$_2$;
Ac-D-hArg(Bu)-Gly-Cys-Phe-D-Trp-Lys-Thr-Cys-Thr-NH$_2$;
Ac-D-hArg(Et)$_2$-Cys-Phe-D-Trp-Lys-Thr-Cys-Thr-NH$_2$;
Ac-L-hArg(Et)$_2$-Cys-Phe-D-Trp-Lys-Thr-Cys-Thr-NH$_2$;
Ac-D-hArg(CH$_2$CF$_3$)$_2$-Cys-Phe-D-Trp-Lys-Thr-Cys-Thr-NH$_2$;
Ac-D-hArg(CH$_2$CF$_3$)$_2$-Gly-Cys-Phe-D-Trp-Lys-Thr-Cys-Thr-NH$_2$;
Ac-D-hArg(CH$_2$CF$_3$)$_2$-Gly-Cys-Phe-D-Trp-Lys-Thr-Cys-Phe-NH$_2$;
Ac-D-hArg(CH$_2$CF$_3$)$_2$-Gly-Cys-Phe-D-Trp-Lys-Thr-Cys-Thr-NHEt;
Ac-L-hArg(CH$_2$—CF$_3$)$_2$-Gly-Cys-Phe-D-Trp-Lys-Thr-Cys-Thr-NH$_2$;
Ac-D-hArg(CH$_2$CF$_3$)$_2$-Gly-Cys-Phe-D-Trp-Lys(Me)-Thr-Cys-Thr-NH$_2$;
Ac-D-hArg(CH$_2$CF$_3$)$_2$-Gly-Cys-Phe-D-Trp-Lys(Me)-Thr-Cys-Thr-NHEt;
Ac-hArg(CH$_3$, hexyl)-Gly-Cys-Phe-D-Trp-Lys-Thr-Cys-Thr-NH$_2$;
H-hArg (hexyl$_2$)-Gly-Cys-Phe-D-Trp-Lys-Thr-Cys-Thr-NH$_2$;
Ac-D-hArg(Et)$_2$-Gly-Cys-Phe-D-Trp-Lys-Thr-Cys-Thr-NHEt;
Ac-D-hArg(Et)$_2$-Gly-Cys-Phe-D-Trp-Lys-Thr-cys-Phe-NH$_2$;
Propionyl-D-hArg(Et)$_2$-Gly-Cys-Phe-D-Trp-Lys(iPr)-Thr-Cys-Thr-NH$_2$;
Ac-D-β-Nal-Gly-Cys-Phe-D-Trp-Lys-Thr-Cys-Gly-hArg(Et)$_2$-NH$_2$;
Ac-D-Lys(iPr)-Gly-Cys-Phe-D-Trp-Lys-Thr-Cys-Thr-NH$_2$;
Ac-D-hArg CH$_2$CF$_3$)$_2$-D-hArg(CH$_2$CF$_3$)$_2$-Gly-Cys-Phe-D-Trp-Lys-Thr-Cys-Thr-NH$_2$;
Ac-D-hArg(CH$_2$CF$_3$)$_2$-D-hArg(CH$_2$CF$_3$)$_2$-Gly-Cys-Phe-D-Trp-Lys-Thr-Cys-Phe-NH$_2$;
Ac-D-hArg(Et)$_2$-D-hArg(Et)$_2$-Gly-Cys-Phe-D-Trp-Lys-Thr-Cys-Thr-NH$_2$;
Ac-Cys-Lys-Asn-4-Cl-Phe-Phe-D-Trp-Lys-Thr-Phe-Thr-Ser-D-Cys-NH$_2$;
H-Bmp-Tyr-D-Trp-Lys-Val-Cys-Thr-NH$_2$;
H-Bmp-Tyr-D-Trp-Lys-Val-Cys-Phe-NH$_2$;
H-Bmp-Tyr-D-Trp-Lys-Val-Cys-p-Cl-Phe-NH$_2$;
H-Bmp-Tyr-D-Trp-Lys-Val-Cys-β-Nal-NH$_2$;
H-D-β-Nal-Cys-Tyr-D-Trp-Lys-Val-Cys-Thr-NH$_2$;
H-D-Phe-Cys-Tyr-D-Trp-Lys-Abu-Cys-Thr-NH$_2$;
H-D-Phe-Cys-Tyr-D-Trp-Lys-Abu-Cys-β-Nal-NH$_2$;
H-pentafluoro-D-Phe-Cys-Tyr-D-Trp-Lys-Val-Cys-Thr-NH$_2$;
Ac-D-β-Nal-Cys-pentafluoro-Phe-D-Trp-Lys-Val-Cys-Thr-NH$_2$;
H-D-β-Nal-Cys-Tyr-D-Trp-Lys-Val-Cys-β-Nal-NH$_2$;
H-D-Phe-Cys-Tyr-D-Trp-Lys-Val-Cys-β-Nal-NH$_2$;
H-D-β-Nal-Cys-Tyr-D-Trp-Lys-Abu-Cys-Thr-NH$_2$;
H-D-p-Cl-Phe-Cys-Tyr-D-Trp-Lys-Abu-Cys-Thr-NH$_2$;
Ac-D-p-Cl-Phe-Cys-Tyr-D-Trp-Lys-Abu-Cys-Thr-NH$_2$;
H-D-Phe-Cys-β-Nal-D-Trp-Lys-Val-Cys-Thr-NH$_2$;
H-D-Phe-Cys-Tyr-D-Trp-Lys-Cys-Thr-NH$_2$;
cyclo(Pro-Phe-D-Trp-N-Me-Lys-Thr-Phe);
cyclo(Pro-Phe-D-Trp-N-Me-Lys-Thr-Phe);
cyclo(Pro-Phe-D-Trp-Lys-Thr-N-Me-Phe);
cyclo(N-Me-Ala-Tyr-D-Trp-Lys-Thr-Phe);
cyclo(Pro-Tyr-D-Trp-Lys-Thr-Phe);
cyclo(Pro-Phe-D-Trp-Lys-Thr-Phe);
cyclo(Pro-Phe-L-Trp-Lys-Thr-Phe);
cyclo(Pro-Phe-D-Trp(F)-Lys-Thr-Phe);
cyclo(Pro-Phe-Trp(F)-Lys-Thr-Phe);
cyclo(Pro-Phe-D-Trp-Lys-Ser-Phe);
cyclo(Pro-Phe-D-Trp-Lys-Thr-p-Cl-Phe);
cyclo(D-Ala-N-Me-D-Phe-D-Thr-D-Lys-Trp-D-Phe);
cyclo(D-Ala-N-Me-D-Phe-D-Val-Lys-D-Trp-D-Phe);
cyclo(D-Ala-N-Me-D-Phe-D-Thr-Lys-D-Trp-D-Phe);
cyclo(D-Abu-N-Me-D-Phe-D-Val-Lys-D-Trp-D-Tyr);
cyclo(Pro-Tyr-D-Trp-t-4-AchxAla-Thr-Phe);
cyclo(Pro-Phe-D-Trp-t-4-AchxAla-Thr-Phe);
cyclo(N-Me-Ala-Tyr-D-Trp-Lys-Val-Phe);
cyclo(N-Me-Ala-Tyr-D-Trp-t-4-AchxAla-Thr-Phe);
cyclo(Pro-Tyr-D-Trp-4-Amphe-Thr-Phe);
cyclo(Pro-Phe-D-Trp-4-Amphe-Thr-Phe);
cyclo(N-Me-Ala-Tyr-D-Trp-4-Amphe-Thr-Phe);
cyclo(Asn-Phe-Phe-D-Trp-Lys-Thr-Phe-Gaba);
cyclo(Asn-Phe-Phe-D-Trp-Lys-Thr-Phe-Gaba-Gaba);
cyclo(Asn-Phe-D-Trp-Lys-Thr-Phe);
cyclo(Asn-Phe-Phe-D-Trp-Lys-Thr-Phe-NH(CH$_2$)$_4$CO);
cyclo(Asn-Phe-Phe-D-Trp-Lys-Thr-Phe-β-Ala);
cyclo(Asn-Phe-Phe-D-Trp-Lys-Thr-Phe-D-Glu)-OH;
cyclo(Phe-Phe-D-Trp-Lys-Thr-Phe);
cyclo(Phe-Phe-D-Trp-Lys-Thr-Phe-Gly);
cyclo(Phe-Phe-D-Trp-Lys-Thr-Phe-Gaba);
cyclo(Asn-Phe-Phe-D-Trp-Lys-Thr-Phe-Gly);
cyclo(Asn-Phe-Phe-D-Trp(F)-Lys-Thr-Phe-Gaba);
cyclo(Asn-Phe-Phe-D-Trp(NO$_2$)-Lys-Thr-Phe-Gaba);
cyclo(Asn-Phe-Phe-Trp(Br)-Lys-Thr-Phe-Gaba);
cyclo(Asn-Phe-Phe-D-Trp-Lys-Thr-Phe(I)-Gaba);
cyclo(Asn-Phe-Phe-D-Trp-Lys-Thr-Tyr(But)-Gaba);
cyclo(Bmp-Lys-Asn-Phe-Phe-D-Trp-Lys-Thr-Phe-Thr-Pro-Cys)-OH;
cyclo(Bmp-Lys-Asn-Phe-Phe-D-Trp-Lys-Thr-Phe-Thr-Pro-Cys)-OH;
cyclo(Bmp-Lys-Asn-Phe-Phe-D-Trp-Lys-Thr-Phe-Thr-Tpo-Cys)-OH;
cyclo(Bmp-Lys-Asn-Phe-Phe-D-Trp-Lys-Thr-Phe-Thr-MeLeu-Cys)-OH;
cyclo(Phe-Phe-D-Trp-Lys-Thr-Phe-Phe-Gaba);
cyclo(Phe-Phe-D-Trp-Lys-Thr-Phe-D-Phe-Gaba);

cyclo(Phe-Phe-D-Trp(5F)-Lys-Thr-Phe-Phe-Gaba);
cyclo(Asn-Phe-Phe-D-Trp-Lys(Ac)-Thr-Phe-NH-(CH$_2$)$_3$—CO);
cyclo(Lys-Phe-Phe-D-Trp-Lys-Thr-Phe-Gaba);
cyclo(Lys-Phe-Phe-D-Trp-Lys-Thr-Phe-Gaba);
cyclo(Orn-Phe-Phe-D-Trp-Lys-Thr-Phe-Gaba);
H-Cys-Phe-Phe-D-Trp-Lys-Thr-Phe-Cys-NH$_2$ (BIM-23268);
H-Cys-Phe-Phe-D-Trp-Lys-Ser-Phe-Cys-NH$_2$ (BIM-23284);
H-Cys-Phe-Tyr-D-Trp-Lys-Thr-Phe-Cys-NH$_2$ (BIM-23295); and
H-Cys-Phe-Tyr(I)-D-Trp-Lys-Thr-Phe-Cys-NH$_2$ (BIM-23313).

Note that for all somatostatin agonists described herein, each amino acid residue represents the structure of —NH—C(R)H—CO—, in which R is the side chain (e.g., CH$_3$ for Ala) except for Thr-ol which means —NH—CH(CH(CH$_3$)OH)—CH$_2$—OH and Pro which means prolinyl. Lines between amino acid residues represent peptide bonds which join the amino acids. Also, where the amino acid residue is optically active, it is the L-form configuration that is intended unless D-form is expressly designated. A disulfide bridge is formed between the two free thiols (e.g., Cys, Pen, or Bmp residues); however, it is not shown.

Use of linear somatostatin agonists of the following formula is also within the invention:

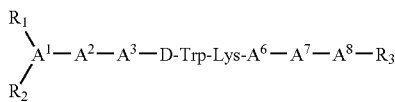

wherein $A^1$ is a D- or L-isomer of Ala, Leu, Ile, Val, Nle, Thr, Ser, β-Nal, β-Pal, Trp, Phe, 2,4-dichloro-Phe, pentafluoro-Phe, p-X-Phe, or o-X-Phe, wherein X is CH$_3$, Cl, Br, F, OH, OCH$_3$ or NO$_2$;

$A^2$ is Ala, Leu, Ile, Val, Nle, Phe, β-Nal, pyridyl-Ala, Trp, 2,4-dichloro-Phe, pentafluoro-Phe, o-X-Phe, or p-X-Phe, wherein X is CH$_3$, Cl, Br, F, OH, OCH$_3$ or NO$_2$;

$A^3$ is pyridyl-Ala, Trp, Phe, β-Nal, 2,4-dichloro-Phe, pentafluoro-Phe, o-X-Phe, or p-X-Phe, wherein X is CH$_3$, Cl, Br, F, OH, OCH$_3$ or NO$_2$;

$A^6$ is Val, Ala, Leu, Ile, Nle, Thr, Abu, or Ser;

$A^7$ is Ala, Leu, Ile, Val, Nle, Phe, β-Nal, pyridyl-Ala, Trp, 2,4-dichloro-Phe, pentafluoro-Phe, o-X-Phe, or p-X-Phe, wherein X is CH$_3$, Cl, Br, F, OH, OCH$_3$ or NO$_2$;

$A^8$ is a D- or L-isomer of Ala, Leu, Ile, Val, Nle, Thr, Ser, Phe, β-Nal, pyridyl-Ala, Trp, 2,4-dichloro-Phe, pentafluoro-Phe, p-X-Phe, or o-X-Phe, wherein X is CH$_3$, Cl, Br, F, OH, OCH$_3$ or NO$_2$;

each $R_1$ and $R_2$, independently, is H, lower acyl or lower alkyl; and $R_3$ is OH or NH$_2$; provided that at least one of $A^1$ and $A^8$ and one of $A^2$ and $A^7$ must be an aromatic amino acid; and further provided that $A^1$, $A^2$, $A^7$ and $A^8$ cannot all be aromatic amino acids.

Examples of linear agonists to be used in the method of this invention include:

H-D-Phe-p-chloro-Phe-Tyr-D-Trp-Lys-Thr-Phe-Thr-NH$_2$;
H-D-Phe-p-NO$_2$-Phe-Tyr-D-Trp-Lys-Val-Phe-Thr-NH$_2$;
H-D-Nal-p-chloro-Phe-Tyr-D-Trp-Lys-Val-Phe-Thr-NH$_2$;
H-D-Phe-Phe-Phe-D-Trp-Lys-Thr-Phe-Thr-NH$_2$ (BIM-23052);
H-D-Phe-Phe-Tyr-D-Trp-Lys-Val-Phe-Thr-NH$_2$;
H-D-Phe-p-chloro-Phe-Tyr-D-Trp-Lys-Val-Phe-Thr-NH$_2$; and
H-D-Phe-Ala-Tyr-D-Trp-Lys-Val-Ala-β-D-Nal-NH$_2$.

If desired, one or more chemical moieties, e.g., a sugar derivative, mono or poly-hydroxy C$_{2-12}$ alkyl, mono or poly-hydroxy C$_{2-12}$ acyl groups, or a piperazine derivative, can be attached to the somatostatin agonist, e.g., to the N-terminus amino acid. See PCT Application WO 88/02756, European Application 0 329 295, and PCT Application No. WO 94/04752. An example of a somatostatin agonists which contain N-terminal chemical substitutions are:

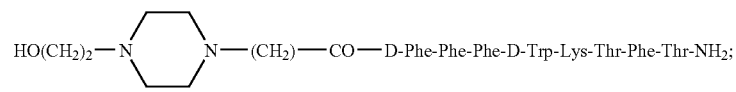

(BIM-23272)

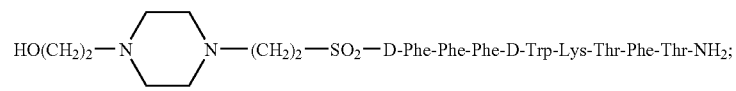

(BIM-23190)

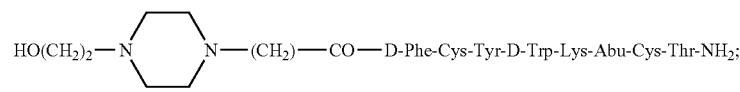

and

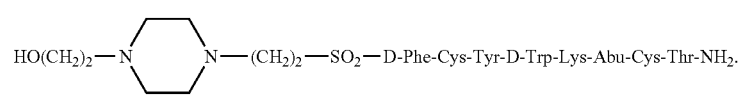

(BIM-23197)

Synthesis of Somatostatin Agonists

The methods for synthesizing somatostatin agonists is well documented and are within the ability of a person of ordinary skill in the art.

Synthesis of short amino acid sequences is well established in the peptide art. For example, synthesis of H-D-Phe-Phe-Phe-D-Trp-Lys-Thr-Phe-Thr-NH$_2$, described above, can be achieved by following the protocol set forth in Example I of European Patent Application 0 395 417 A1. The synthesis of somatostatin agonists with a substituted N-terminus can be achieved, for example, by following the protocol set forth in WO 88/02756, European Patent Application No. 0 329 295, and PCT Publication No. WO 94/04752.

Somatostatin Receptor Binding Assays

The human SSTR-1, SSTR-2, SSTR-3, SSTR-4, and SSTR-5 cDNA clones have been described (SSTR-1 and SSTR-2 in Yamada, Y., et al., Proc. Natl. Acad. Sci. USA, 89:251-255 (1992); SSTR-3 in Yamada, et al., Mol. Endocrinol. 6:2136-2142 (1993); and SSTR-4 and SSTR-5 in Yamada, et al., Biochem. Biophys. Res. Commun. 195:844-852 (1993)) and are also available from American Type Culture Collection (ATCC, Rockville, Md.) (ATCC Nos. 79044 (SSTR-1), 79046 (SSTR-2) and 79048 (SSTR-3)). Based on the restriction endonuclease maps, the entire coding region of each SSTR cDNA may be excised by suitable restriction endonuclease digestion (Maniatis, T., et al., *Molecular Cloning—A Laboratory Manual, CSHL,* 1982). Restriction endonucleases are available from New England Biolabs (Beverly, Mass.). This cDNA fragment was inserted into the mammalian expression vector, pCMV (Russell, D., et al., J. Biol. Chem., 264:8222-8229 (1989)), using standard molecular biology techniques (see e.g., Maniatis, T., et al., Molecular Cloning, —A Laboratory Manual, Cold Spring Harbor Laboratory, 1982) to produce the expression plasmid, pCMV-human SSTR-1 through pCMV-human SSTR-5. Other mammalian expression vectors include pcDNA1/Amp (Invitrogen, Sandlesy, Calif.). The expression plasmids were introduced into the suitable bacterial host, *E. Coli* HB101 (Stratagene, La Jolla, Calif.) and plasmid DNAs, for transfection, were prepared on Cesium Chloride gradients.

CHO-K1 (ovary, Chinese hamster) cells were obtained from ATCC (ATCC No. CCL 61). The cells were grown and maintained in Ham's F12 media (Gibco BRL, Grand Island, N.Y.) supplemented with 10% fetal bovine serum under standard tissue culture conditions. For transfection, the cells were seeded at a density 1×10$^6$/60-cm plate (Baxter Scientific Products, McGaw Park, Ill.). DNA mediated transfection was carried out using the calcium phosphate co-precipitation method (Ausubel, F. M., et al., Current Protocols in Molecular Biology, John Wiley & Sons, 1987). The plasmid pRSV-neo (ATCC; ATCC No. 37198) was included as a selectable marker at 1/10 the concentration of the expression plasmid. CHO-K1 clonal cell lines that have stably inherited the transfected DNA were selected for growth in Ham's F12 media containing 10% fetal bovine serum and 0.5 mg/ml of G418 (Sigma). The cells were ring-cloned and expanded in the same media for analysis.

Expression of the human SSTR-1 through SSTR-5 receptors in the CHO-K1 cells were detected by Northern blot analysis of total RNA prepared from the cells (Sambrook, J. E., et al., Molecular Cloning—A Laboratory Manual, Ed. 2., Cold Spring Harbor Laboratory, Cold Spring Harbor, N.Y., 1989) and by receptor binding using [$^{125}$I-Tyr$^{11}$]somatostatin-14 as a ligand. Transfected cell lines expressing the human SSTR receptors were clonally expanded in culture and used in the following SSTR binding protocol.

Crude membranes were prepared by homogenization of the transfected cells in 20 ml of ice-cold 50 mM Tris-HCl with a POLYTRON homogenizer (setting 6, 15 sec). Buffer was added to obtain a final volume of 40 ml, and the homogenate was centrifuged in a Sorval SS-34 rotor at 39,000 g for 10 min at 0-4° C. The resulting supernatant was decanted and discarded. The pellet was rehomogenized in ice-cold buffer, diluted, and centrifuged as before. The final pellet was resuspended in the 10 mM Tris HCl and held on ice for the receptor binding assay.

Aliquots of the membrane preparation were incubated for 30 min at 30° C. with 0.05 nM [$^{125}$I-Tyr$^{11}$]somatostatin-14 (2000 Ci/mmol; Amersham Corp., Arlington Heights, Ill.) in 50 mM HEPES (pH 7.4) containing a test somatostatin agonist of various concentrations (e.g., $10^{-11}$ to $10^{-6}$), 10 mg/ml bovine serum albumin (fraction V) (Sigma Chemical Co., St. Louis, Mo.), MgCl$_2$ (5 mM), Trasylol (200 KIU ml), bacitracin (0.02 mg/ml), and phenylmethylsulphonyl fluoride (0.02 mg/ml). The final assay volume was 0.3 ml. The incubations were terminated by rapid filtration through GF/C filters (pre-soaked in 0.3% polyethylenimine for 30 min) using a Brandel filtration manifold. Each tube and filter were then washed three times with 5 ml aliquots of ice-cold buffer. Specific binding was defined as the total [$^{125}$I-Tyr$^{11}$]SRIF-14 bound minus that bound in the presence of 1000 nM. The Ki values for the tested somatostatin agonists were calculated by using the following formula: Ki=IC$_{50}$/[1+(LC/LEC)] where IC$_{50}$ is the concentration of test somatostatin agonist required to inhibit 50 percent of the specific binding of the radioligand [$^{125}$I-Tyr$^{11}$] somatostatin-14, LC is the concentration of the radioligand (0.05 nM), and LEC is the equilibrium dissociation constant of the radioligand (0.16 nM). The Ki values (nm) for the tested somatostatin agonists are shown in Table I.

TABLE I

|  | hSSTR-1 | hSSTR-2 | hSSTR-3 | hSSTR-4 | hSSTR-5 |
| --- | --- | --- | --- | --- | --- |
| Somatostatin-14 | 2.26 | 0.23 | 1.2 | 1.8 | 1.41 |
| Somatostatin-28 | 2.38 | 0.30 | 1.3 | 7.93 | 0.4 |
| Octreotide | 875 | 0.57 | 26.8 | 5029 | 6.78 |
| BIM-23014 | 2414 | 0.75 | 97.9 | 1826 | 5.21 |
| BIM-23052 | 97.6 | 11.96 | 5.6 | 127 | 1.22 |
| BIM-23190 | 9120 | 0.35 | 215 | 7537 | 11.1 |
| BIM-23197 | 6016 | 0.19 | 26.8 | 3897 | 9.81 |
| BIM-23272 | 47.7 | 3.23 | 10.9 | 753 | 1.01 |
| BIM-23284 | 27.9 | 19.3 | 35.6 | 58.6 | 0.85 |
| BIM-23295 | 86.9 | 6.19 | 9.7 | 3.4 | 0.34 |
| BIM-23313 | 15.1 | 4.78 | 25.5 | 55.3 | 0.30 |
| BIM-26268 | 1227 | 15.06 | 545 | 3551 | 0.42 |

Insulin Sensitivity Studies

The effect of chronic (one week) treatment with BIM-23268 on insulin sensitivity was examined in an obese hyperinsulinemic, insulin resistant animal model, the fatty (fa/fa) Zucker rats (Bray, G., Federation Proceedings 36:148-153 (1977); Shafris, E., Diabetes/Metab. Rev. 8:179-208 (1992)). Male fatty Zucker rats (Harlan-Olac, Bicester, Oxon, U.K.), which were 15-17 weeks old, were randomly divided into two groups. The animals were house in pairs in a normal 12 hour light:12 hour darkness cycle at 20±2° C. and fed a standard laboratory rat diet (Beekay rat and mouse diet, Bantin & Kingman, Hull, Humberside, U.K.) ad libitum. For the group assigned to receive drug treatment, the rats received BIM-23268C at 3 mg/kg, by subcutaneous injection, twice a day at 10:00 AM and 5:00 PM. The other group, the control group, was treated with a subcutaneous injection of 0.1 ml/100 g of saline twice a day at 10:00 AM and 5:00 PM. The animals were subjected to the BIM-23268 or saline treatment for a total of 7 days. On the last day of treatment, at 5:00 PM food was removed, and the rats were fasted overnight.

A method for assessing insulin sensitivity is to administer an oral glucose challenge and monitoring the secretion of insulin and disposal of glucose from the blood stream over a 240 min period (Bergman, R. N., et al., Endocrine Review 6:45-86 (1985)). At 9:00 AM the next day, both control and BIM-23268 treated animals were administered a 0.8 grams/kg body weight glucose challenge at 0 minutes. 20 µl blood samples were taken from tail vein (Abdel-Halim, S. M., et al., Diabetes 43:281-288 (1994)) at −60 min, −30 min, 0 min, 30 min, 60 min, 90 min, 120 min, and 240 min.

The 20 µl samples were taken into 380 µl of hemolysis reagents (Sigma, Poole, Dorset, UK) containing 50 mg/liter of digitonin (Cat# D-1407) and 100 mg/liter of Maleimide (M-3766). From this, 100 µl of the hemolysed blood sample was added to 0.9 ml of Tinder reagent (Sigma Enzymatic calorimetric assay for blood glucose, Cat# 315-100, Sigma Chemical Co. Ltd, Poole, Dorset, UK). Blood glucose was determined according to vendor's recommendation at 505 nm.

Insulin was measured by the conventional radioimmunoassay method as described (Dunmore, S., & Beloff-Chain, A., J Endocrinol. 92:15-21 (1982)). Samples were assayed in triplicates with a 1:30000 dilution of an insulin antiserum (from guinea pig)raised in the laboratory (Dunmore, S. J., et al., J. Endocrinol. 137:375-381 (1993), and using $^{125}$I-labelled bovine insulin, iodinated by the chloramine T method (Sambrook, et al., Molecular Cloning—A Laboratory Manual, Ed. 2., Cold Spring Harbor Laboratory Press, 1989). Rat insulin (2000U/0.1 ml, Novo Nordisk Laboratories, Basingstoke, Hants, U.K.) was used as a standard in the assay. The standards and samples were diluted in assay buffer containing NaH2PO4 5.7 g/L, bovine serum albumin (Sigma A4378, Sigma Chemical Co. Ltd., Poole, Dorset, UK) 5.0 g/L, NaN3 1.0 g/L buffered to pH 7.4). Antibody-bound insulin was separated on from free insulin by the addition of a second antibody (donkey anti-guinea pig Ig) coated on cellulose, Sac-Cel (IDS, Boldon, Tyne & Wear, UK). The antibody-bound insulin precipitate was separated by centrifugation. Counts bound were measured on an LKB Rackgamma solid scintillation counter.

Although the fatty Zucker rats in the control (saline treated) group were insulin resistant, they were not hyperglycemic (~5 mM ambient plasma glucose concentration at time −60 min, −30 min and 0 min, after an overnight fast) because the prevailing hyperinsulinemic state (2-3 nmol/L after an overnight fast) of these animals compensated for the reduction in glucose disposal rate in peripheral tissues. This is evident in the plasma glucose curve and the insulin response during a glucose challenge. Thus, any normal suppression of plasma insulin in these animals should result in an impairment of glucose tolerance after a glucose challenge. The BIM-23268 treated group, examined after 7 days of treatment with agent by subcutaneous injection at 3 mg/kg, twice daily, showed a significant suppression of glucose stimulated insulin secretion to the glucose challenge. Despite an inhibition of pancreatic insulin response to the glucose challenge, the BIM-23268-treated animals did not show an impairment in glucose tolerance. The plasma glucose profile of the treatment group was not significantly different from that in the untreated group. Taken together, the results demonstrate that BIM-23268 treatment, while suppressing hyperinsulinemia, produced an improvement in insulin-sensitivity.

Weight Loss Studies

The effect of chronic (6 day) treatment with BIM-23268 on body weight gain/loss was examined in an obese animal model, the fatty (fa/fa) Zucker rats (purchased from Harlan-Olac, Bicester, Oxon, U.K. See Bray, G., Federation Proceedings 36:148-153 (1977). Eleven male fatty Zucker rats weighing about 450 grams were randomly divided into two groups, and their initial body weights recorded. The animals were housed in pairs in a normal 12 hour light:12 hour darkness cycle at 20±2° C. and fed overnight ad libitum.

For the group assigned to receive drug treatment, the rats received the type-5 somatostatin receptor selective agonist BIM-23268C at 3 mg/kg, by subcutaneous injection twice a day at 10:00 a.m. and 5:00 p.m. The other group was treated with a subcutaneous injection of 0.1 ml/100 g of saline twice a day at 10:00 a.m. and 5:00 p.m. The animals were subjected to the BIM-23268 or saline treatment for a total of six days.

At 10:00 a.m. each day, food was removed and replaced with accurately weight 100 gram food pellet (a standard laboratory rat diet, Beekay rat and mouse diet, Bantin & Kingman, Hull, Humberside, U.K.). The amount of food remaining a 10:00 a.m. the next day was accurately weighed, recorded and replaced with 100 grams of fresh food pellets.

The animals were weighed each day during the 6-day treatment period at 5:00 p.m. The untreated control group mean weight was 414.09 at the start of the trial and was 418.89 after six days. The BIM-23268 treated group's mean weight was 413.6 at the start of the trial and remained at 413.6 after six days. The average food consumption for the control group was 26.0 g/rat/day and for the BIM-26268 group was 25.9 g/rat/day.

These results showed that body weight gain was lower in animals treated with BIM-23268. The effect on body weight change was not due to a toxic effect of the agent, as the treated group appeared healthy, and there was no difference in the amount of food consumed over the entire treatment period.

Lipidemia Studies

Obese (fa/fa) Zucker rats were treated as in example 1 above. On the last day of treatment (day 6), food was removed at 5:00 p.m., and the rats were fasted overnight. At 9:00 a.m. the next day, the animals were subjected to a glucose challenge, given as 0.8 gram/kg of glucose orally. Periodic 400 µl of blood samples were taken from the tail vein (Peterson, R. G., ILAR News, 32:16-19 (1990)) 60 min. and 30 min. before and at 30, 60, 90, and 120 min. after the administration of the glucose challenge (0.8 gram/kg orally). Aprotinin (Traysylol, Bayer UK, Hayward's Health, W. Sussex, U.K.) and heparin (Sigma Chemical Co., Poole, Dorset, U.K.) were added to the blood samples to a final concentration of 400 KIU/ml and 100 units/ml, respectively. Plasma fractions were prepared from these samples by centrifugation at 4000×G in a microfuge, for the estimation of triglycerides and glycerol. Samples were then stored at −80° C. until assayed.

Plasma glycerol and triglycerides were determined using the Sigma Enzymatic (Tinder) calorimetric assay kit (Cat #337-B, Sigma Chemical Co., Poole, Dorset, U.K.) and measuring absorbance at 540 nm in a spectrophotometer.

After six days of treatment with BIM-23268C at 3 mg/kg twice a day by subcutaneous injection, both plasma glycerol and triglycerides were significantly lowered, as exemplified by the samples taken 30 and 60 minutes before the oral glucose challenge. The administration of an oral glucose challenge has no significant effect on plasma lipids. The BIM-23628C treated group showed a significantly lower plasma glycerol and triglycerides throughout the 2-hour test period. The results suggested that BIM-23268C, following a 6-day treatment period at the prescribed dose, was effective in reducing hypertriglyceridemia.

Other Embodiments

The foregoing description has been limited to specific embodiments of this invention. It will be apparent, however, that variations and modifications may be made to the invention, with the attainment of some or all of the advantages of the invention. Such embodiments are also within the scope of the following claims.

---

The invention claimed is:

1. A method of decreasing insulin resistance in a patient, said method comprising administering to said patient a therapeutically effective amount of H-Cys-Phe-Phe-D-Trp-Lys-Thr-Phe-Cys-NH$_2$, wherein a disulfide bond exists between the free thiols of two Cys residues.

2. The method according to claim 1 wherein said patient is a non-insulin-dependent diabetic.

3. A method decreasing Syndrome X in a patient, said method comprising the steps of administering to said patient a therapeutically effective amount of H-Cys-Phe-Phe-D-Trp-Lys-Thr-Phe-Cys-NH$_2$, wherein a disulfide bond exists between the free thiols of two Cys residues, to said patient; repeatedly administering to said patient a therapeutically effective amount of H-Cys-Phe-Phe-D-Trp-Lys-Thr-Phe-Cys-NH$_2$, wherein a disulfide bond exists between the free thiols of two Cys residues, to said patient until such time as an improvement in the health of said patient is observed wherein said improvement consists essentially of a restoration of insulin sensitivity, lower plasma lipid levels, a decrease blood pressure and or a redistribution of body fat.

4. The method according to claim 3 wherein said patient is a non-insulin-dependent diabetic.

5. The method according to claim 3 wherein said redistribution of said body fat of said patient is accomplished by a weight loss in said patient.

* * * * *